United States Patent
Lifshitz-Liron et al.

(10) Patent No.: US 7,358,360 B2
(45) Date of Patent: Apr. 15, 2008

(54) RISEDRONATE SODIUM HAVING A VERY LOW CONTENT OF IRON

(75) Inventors: Revital Lifshitz-Liron, Herzlia (IL); Ramiy Lidor-Hadas, Kfar Saba (IL); Nissm Sasson, Or Akiva (IL); Igor Lifshitz, Petach-Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 758 days.

(21) Appl. No.: 10/759,919

(22) Filed: Jan. 16, 2004

(65) Prior Publication Data

US 2004/0192655 A1    Sep. 30, 2004

Related U.S. Application Data

(60) Provisional application No. 60/445,139, filed on Feb. 5, 2003, provisional application No. 60/441,062, filed on Jan. 17, 2003.

(51) Int. Cl.
*C07F 9/28* (2006.01)

(52) U.S. Cl. .......................................... 546/22

(58) Field of Classification Search ..................... None
See application file for complete search history.

(56) References Cited

U.S. PATENT DOCUMENTS

| | | | |
|---|---|---|---|
| 6,410,520 B2 * | 6/2002 | Cazer et al. .................. | 514/89 |
| 2003/0195170 A1 | 10/2003 | Aronhime et al. | |
| 2006/0110452 A1 * | 5/2006 | Dansereau et al. ......... | 424/464 |

FOREIGN PATENT DOCUMENTS

WO    WO 01/56983 A2 *    8/2001

OTHER PUBLICATIONS

Encyclopedia of Chemical Technology, Fourth Edition, vol. 5, 1993, pp. 764-795.
Encylcopedia of Chemical Technology, Fourth Edition, vol. 14, 1995, pp. 887-892.

* cited by examiner

*Primary Examiner*—Raymond J. Henley, III
(74) *Attorney, Agent, or Firm*—Kenyon & Kenyon LLP

(57) ABSTRACT

The present invention relates to a method of making risedronate sodium substantially free of iron including the steps of refluxing, especially with mechanical agitation, a combination of risedronic acid, a sodium base, especially sodium hydroxide, and an iron-reducing amount of EDTA in a liquid that is water, a lower alkanol, or, especially, a mixture of a lower alkanol and water; and isolating risedronate sodium substantially free of iron from the combination.

17 Claims, No Drawings

RISEDRONATE SODIUM HAVING A VERY LOW CONTENT OF IRON

This application claims the benefit of U.S. Provisional Patent Application 60/441,062 filed Jan. 17, 2003 and U.S. Provisional Patent Application 60/445,139 filed Feb. 5, 2003, both of which are incorporated herein by reference.

BACKGROUND OF THE INVENTION

Risedronate sodium [1-hydroxy-3-(3-pyridinyl)ethylidene-bisphosphonic acid sodium salt] is known to be useful in the treatment of diseases, like osteoporosis, characterized by progressive loss of bone mineral and architectural deterioration of bone tissue. The present inventors have observed that risedronate sodium is prone to pick-up or retain metals, especially iron, during synthesis and work-up.

Phosphonates, i.e. compounds containing one or more groups of structure $C-P(O)(OH)_2$, can function as chelating agents. A chelating agent is a multidentate ligand. It simultaneously attaches to two or more positions in the coordination sphere of the central metal ion. Without being held to any theory of operation, the present inventors believe that risedronate sodium can act as a chelating agent, which contributes to the pick-up and retention of metals, especially iron.

Residual iron is unnecessary and does not contribute to the pharmacological efficacy of risedronate sodium. Residual iron correlates with yellowness in the product, which is an undesirable quality in a pharmaceutical compound. Clearly, there is a need for methods to obtain sodium risedronate with a very low content of residual iron and with a corresponding excellent color.

Risedronate sodium is also capable of existing in several polymorphic or pseudopolymorphic forms. The polymorphs and pseudopolymorphs can be influenced by controlling the conditions under which the salt is obtained in solid form, for example by controlling conditions of crystallization. Solid state physical properties that can differ from one polymorph (or pseudopolymorph) to the next include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch, or tribasic calcium phosphate. Clearly, discovery of new polymorphs or pseudopolymorphs and control of polymorphic form are desirable.

SUMMARY OF THE INVENTION

In one aspect, the present invention relates to a method of making risedronate sodium substantially free of iron including the steps of refluxing, especially with mechanical agitation, a combination of risedronic acid, a sodium base, especially sodium hydroxide, and an iron-reducing amount of EDTA in a liquid that is water, a lower alkanol, or, especially, a mixture of a lower alkanol and water; and isolating risedronate sodium substantially free of iron from the combination.

In another aspect, the present invention relates to a method of making risedronate sodium form B substantially free of iron including the steps of refluxing, especially with mechanical agitation, a combination of risedronic acid, a sodium base, especially sodium hydroxide, and an iron-reducing amount of EDTA in a liquid that is water, a lower alkanol, or, especially, a mixture of a lower alkanol and water; and isolating risedronate sodium form B substantially free of iron from the combination.

In yet another aspect, the present invention relates to risedronate sodium made by the claimed process.

In another aspect, the present invention relates to a method of treating bone loss by administering a pharmaceutical formulation containing risedronate sodium made by the claimed process.

In another aspect, the present invention relates to risedronate sodium substantially free of iron.

DETAILED DESCRIPTION OF THE INVENTION

As used herein, risedronate sodium refers to the monosodium salt of risedronic acid, i.e., 1-hydroxy-2(3-pyridinyl) ethylidene bis phosphonic acid monosodium salt. Risedronate sodium has the empirical formula $C_7H_{10}NO_7P_2Na$.

Unless otherwise required by the context, as used herein risedronate sodium refers to risedronate sodium in any polymorphic or pseudopolymorphic form, as well as amorphous material.

As used herein in connection with a measured quantity, the term "about" indicates that variation in the measured quantity as would be expected by the skilled artisan making the measurement or determination and exercising a level of care commensurate with the objective of the measurement and the precision of the measuring apparatus being used.

As used herein, risedronate sodium form B refers to risedronate sodium having at least one characteristic of form B. Form B can be characterized by either its X-ray diffraction pattern or its FTIR spectrum as described in the U.S. patent application Ser. No. 10/337,676 filed Jan. 6, 2003.

As used herein, "residual iron" is iron that is unnecessary to risedronate sodium and does not contribute to the pharmacological efficacy of risedronate sodium.

As used herein, the term lower alkanol refers to compounds of the general formula ROH, where R is a linear or branched alkyl group having up to 6 carbon atoms. Methanol, ethanol, and iso-propanol are preferred lower alkanols. Ethanol is a particularly preferred lower alkanol for use in the practice of the present invention.

As used herein in connection with liquids that are mixtures, v/v and volume/volume refer to the ratio of volumes of liquids (e.g. alcohols and water) that are combined to make the liquid. Thus, 50/50, v/v, refers to a mixture made by combining approximately equal volumes of two liquids.

As used herein, sodium base refers to a base, like sodium hydroxide, having sodium as a cation. Many such bases are known to the skilled artisan. Sodium hydroxide is a preferred sodium base in the practice of the present invention.

The iron content of risedronate sodium as discussed herein was measured by the technique of inductively coupled plasma atomic emission spectroscopy (hereafter "AES").

As used herein, "substantially free of iron" means that the risedronate sodium substantially free of iron contains at least about 30% less of the iron than the risedronate sodium made by the same process and using the same materials, but without an iron-reducing amount of EDTA, e.g. the process of Example 2, Preparation B. Preferably, risedronate sodium substantially free of iron contains at least about 30% to about 50% less iron than risedronate sodium made by the same process and using the same materials, but without an iron-reducing amount of EDTA, e.g. the process of Example 2, Preparation B.

Risedronate sodium substantially free of iron preferably contains less than about 50 parts per million (ppm) of iron as determined by AES.

In one embodiment, the present invention relates to a method of making risedronate sodium that is substantially free of iron that includes the step of refluxing a combination of risedronic acid, a sodium base, and an iron-reducing amount of edetic acid (ethylenediaminetetraacetic acid, EDTA) in a liquid that is water, a lower alkanol, or, preferably, a mixture of water and a lower alkanol. A preferred liquid is made-up of about 40% to about 60%, v/v, of a lower alkanol in water. A more preferred liquid is made-up of about 50%, v/v, of a lower alkanol in water.

The ratio of the number of moles of risedronic acid to the number of moles of sodium base is between about 1:0.8 and about 1:1.2, preferably between about 1:1 and about 1:1.2. The skilled artisan will know to adjust this ratio if a multifunctional sodium base is used (i.e. a sodium base capable of reacting with more than one mole of a acid). Preferably, the entire amount of sodium base is not added at once. Rather, it is added in small portions (e.g. dropwise) at reflux, preferably with mechanical agitation, as a solution in a liquid to a refluxing combination of risedronic acid, an iron-reducing amount of EDTA, and liquid that can be water, a lower alkanol, or a mixture of water and a lower alkanol. Depending on the composition of the liquid and the temperature, more or less of the EDTA may dissolve. It is convenient but not necessary if the liquid in which the sodium base is dissolved has approximately the same composition as the liquid in which risedronic acid is suspended at reflux.

The EDTA is used in an iron-reducing amount which is an amount such that risedronate sodium that is substantially free of iron is obtained from the process. The iron-reducing amount is an amount such that the risedronate sodium substantially free of iron contains at least about 30% less of the iron than the risedronate sodium made by the same process and using the same materials, but without an iron-reducing amount of EDTA, e.g. the process of Example 2, Preparation B. In particular, the iron-reducing amount is an amount such that the risedronate sodium substantially free of iron contains less than 50 ppm of iron. The amount of EDTA used will generally be between about 5% and about 50%, preferably between about 5% and 20%, on a dry per-weight basis, of the risedronic acid used. The skilled artisan will know to adjust this value through routine experimentation, depending on the amount of iron, which can be determined by techniques well known in the art.

The combination of risedronic acid, sodium base, and EDTA is maintained at reflux for a time sufficient to ensure a good yield of risedronate sodium. Preferably, the combination is refluxed until the pH is between about 4 and about 5, preferably between about 4.2 and about 4.7. The combination is subjected to shear forces, for example by a stirrer or mechanical agitation, during reflux. Mechanical agitation can be overhead paddle-type agitation or magnetic agitation, to mention just two.

After reflux, the mixture is cooled to obtain risedronate sodium. Preferably, the cooling is to a temperature between about 0° C. and about 30° C. After cooling, risedronate sodium substantially free of iron is isolated by any means known in the art, for example filtration (gravity or suction) or centrifugation, to mention just two.

After isolating, the product obtained can be washed with water, a lower alkanol, or a mixture of a lower alkanol and water. The composition of the wash liquid can be the same as that of the reflux liquid or it can be different. The product can be further washed with lower alkanol, preferably ethanol.

The risedronate sodium obtained through the practice of the present invention is substantially free of iron and has excellent color. The color of the risedronate sodium can be evaluated by methods known in the art, for example, an APHA color test.

In preferred embodiments, especially when the liquid is made-up of 50%, v/v, ethanol in water, the risedronate sodium substantially free of iron is risedronate sodium form B, which can be characterized by x-ray diffraction peaks (reflections) at 2θ values of about 6.0, 14.4, 19.6, 24.9, and 25.4±0.2 degrees, or by FTIR absorption bands at about 624, 951, 796, 912, 931, 1046, 1105, 1123, 1323, and 1641 cm$^{-1}$. Form B is a monohydrate as proved by single crystal x-ray analysis.

Risedronate sodium of the invention can be used in the form of pharmaceutical compositions which are prepared by using diluents or excipients such as carriers, fillers, bulking agents, binders, wetting agents, disintegrating agents, surface active agents, lubricants, and the like. For the pharmaceutical compositions, various types of administration unit forms can be selected depending on the therapeutic purpose, for example tablets, pills, powders, liquids, suspensions, emulsions, granules, capsules, suppositories, injection preparations (solutions and suspensions), and the like. Any excipient commonly known and used widely in the art can be used in the pharmaceutical composition. Carriers include, but are not limited to, lactose, white sugar, sodium chloride, glucose, urea, starch, calcium carbonate, kaolin, crystalline cellulose, and silicic acid. Binders include, but are not limited to, water, ethanol, propanol, simple syrup, glucose solutions, starch solutions, gelatin solutions, carboxymethyl cellulose, shelac, methyl cellulose, potassium phosphate, and polyvinylpyrrolidone. Disintegrating agents include, but are not limited to, dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, and lactose. Disintegration inhibitors include, but are not limited to, white sugar, stearin, coconut butter, and hydrogenated oils. Absorption accelerators include, but are not limited to, quaternary ammonium base and sodium laurylsulfate. Wetting agents include, but are not limited to, glycerin and starch. Adsorbing agents include, but are not limited to, starch, lactose, kaolin, bentonite, and colloidal silicic acid. Lubricants include, but are not limited to, purified talc, stearates, boric acid powder, and polyethylene glycol. Tablets can be further coated with commonly known coating materials such as sugar coated tablets, gelatin film coated tablets, tablets coated with enteric coatings, tablets coated with films, double layered tablets, and multi-layered tablets.

When shaping the pharmaceutical composition into pill form, any commonly known excipient used in the art can be used. For example, carriers include, but are not limited to, lactose, starch, coconut butter, hardened vegetable oils, kaolin, and talc. Binders include, but are not limited to, gum arabic powder, tragacanth gum powder, gelatin, and ethanol. Disintegrating agents include, but are not limited to, agar, and laminalia.

For the purpose of shaping the pharmaceutical composition in the form of suppositories, any commonly known excipient used in the art can be used. For example, excipients include, but are not limited to, polyethylene glycols, coconut butter, higher alcohols, esters of higher alcohols, gelatin, and semisynthesized glycerides.

When preparing injectable pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added. If necessary, coloring agents, preservatives, perfumes, seasoning agents, sweetening agents, and other medicines may also be added to the desired preparations.

The amount of risedronate sodium contained in a pharmaceutical composition is not specifically restricted, however, the dose should be sufficient to treat, ameliorate, or reduce the symptoms associated with bone loss.

Methods of administration of a pharmaceutical composition for treating bone loss of the present invention are not specifically restricted, and can be administered in various preparations depending on the age, sex, and symptoms of the patient. For example, tablets, pills, solutions, suspensions, emulsions, granules and capsules may be orally administered. Injection preparations may be administered individually or mixed with injection transfusions such as glucose solutions and amino acid solutions intravenously. If necessary, the injection preparations are administered singly intramuscularly, intracutaneously, subcutaneously or intraperitoneally. Suppositories may be administered into the rectum.

The dosage of a pharmaceutical composition for treating bone loss according to the present invention will depend on the method of use, the age, sex, and condition of the patient.

The present invention is further illustrated with the following non-limiting examples.

EXAMPLE 1

A solution of sodium hydroxide (7.4 g, 1 eq.) in a mixture of water/ethanol (50%, v/v) (150 ml) was added drop-wise to a suspension of risedronic acid (50 g) and 5 g of EDTA (ca. 10% on a dry per-weight basis) in a mixture of water/ethanol (50%, v/v) (850 ml) at reflux temperature. The reaction mixture was stirred at reflux temperature until the pH was stable at about 4.2-4.7. The reaction mixture was cooled to a temperature of about 50° C. The precipitate was then filtered, washed twice with 50 ml mixture of water/ethanol (50%, v/v) and then with ethanol (1×50 ml) and dried over night at 50° C. to give 48.5 g (85%) of sodium risedronate white crystal substance of form B (water content by thermogravimetric analysis was 5.5%-7.5%). Less than 50 ppm of iron was found in the product by AES.

EXAMPLE 2

Two replicate preparations of risedronate sodium from risedronic acid and sodium hydroxide in a reflux solvent (water/ethanol, 50/50, v/v) are carried out following the general procedure of Example 1. In one preparation (A), EDTA is included (15% by weight based on the dry weight of risedronic acid). In the other preparation (B), no EDTA is used. The reaction, isolation, and work-up are as in Example 1. The residual metals content of the products are analyzed by AES with the results summarized in Table 1.

EXAMPLE 3

A solution of sodium hydroxide (7.4 g, 1 eq.) in a mixture of water/ethanol (50%, v/v) (150 ml) was added dropwise to a suspension of risedronic acid (50 g) and 5 g of EDTA (ca. 10% on a dry per-weight basis) in a mixture of water/ethanol (50%, v/v) (850 ml) at reflux temperature. The reaction mixture was stirred at reflux temperature until the pH was stable at about 4.2-4.7. The reaction mixture was cooled to a temperature of about 22° C. The precipitate was then filtered, washed twice with 50 ml mixture of water/ethanol (50%, v/v) and then with ethanol (1×50 ml) and dried over night at 50° C. to give 48.5 g (85%) of sodium risedronate white crystal substance of form B (water content by thermogravimetric analysis was 5.5%-7.5%). Less than 50 ppm of iron was found in the produce by AES.

EXAMPLE 4

Two replicate preparations of risedronate sodium from risedronic acid and sodium hydroxide in a reflux solvent (water/ethanol, 50/50, v/v) are carried out following the general procedure of Example 1. In one preparation (A), EDTA is included (10% by weight based on the dry weight of risedronic acid). In the other preparation (B), no EDTA is used. The reaction, isolation, and work-up are as in Example 1. The iron content of the products are analyzed by AES with the results summarized in Table 1.

TABLE 1

|  | EDTA | Iron content |
|---|---|---|
| Risendronic acid (raw material) | — | 55 ppm |
| Preparation A | 10% w/w | 12 ppm |
| Preparation B | None | 38 ppm |

What is claimed is:

1. A method of making risedronate sodium, substantially free of iron, comprising:
    refluxing a combination comprising risedronic acid, a sodium base, and an iron-reducing amount of EDTA in a liquid; and
    isolating risedronate sodium substantially free of iron from the combination.

2. The method of claim 1, wherein the sodium base is sodium hydroxide.

3. The method of claim 1, wherein the sodium base in the combination is of an amount such that the ratio of the number of moles of sodium base to the number of moles of risedronic acid in the combination is between about 1:0.8 and about 1:1.2.

4. The method of claim 3, wherein the ratio of moles of sodium base to moles of risedronic acid is between about 1:1 and 1:1.2.

5. The method of claim 1, wherein the iron-reducing amount of EDTA is between about 5% and about 50% of the risedronic acid on a dry per-weight basis.

6. The method of claim 5, wherein the iron-reducing amount of EDTA is between about 5% and about 20% of the risedronic acid on a dry per-weight basis.

7. The method of claim 1, wherein the liquid is selected from the group consisting of water, a lower alkanol, and a mixture of a lower alkanol and water.

8. The method of claim 7, wherein the liquid is about 40% to about 60%, v/v, of a lower alkanol in water.

9. The method of claim 8, wherein the liquid is about 50%, v/v, of a lower alkanol in water.

10. The method of claim 1, wherein the combination is refluxed until the pH is between about 4 and about 5.

11. The method of claim 10, wherein the combination is refluxed until the pH is between about 4.2 and about 4.7.

12. The method of claim 1, wherein during the refluxing step, the combination is subjected to shear forces.

13. The method of claim 12, wherein during the refluxing step, the combination is subjected to mechanical agitation.

14. The method of claim 1, further comprising cooling the refluxed combination after the refluxing step.

15. The method of claim 14, wherein the refluxed combination is cooled to a temperature between about 0° C. and about 30° C.

16. The method of claim 1, wherein the amount of metal in the isolated risedronate sodium is at least about 30% to about 50% lower than the amount of metal in risedronate sodium made by the method of claim 1 without a metal-reducing amount of EDTA.

17. The method of claim 1, wherein the liquid is a mixture of ethanol and water, and the obtained risedronate sodium is crystalline Form B.

* * * * *